(12) United States Patent
Seim et al.

(10) Patent No.: US 11,877,849 B1
(45) Date of Patent: Jan. 23, 2024

(54) DEVICE AND METHOD TO ASSESS HAND FLEXION TONE

(71) Applicant: The Board of Trustees of the Leland Stanford Junior University, Stanford, CA (US)

(72) Inventors: Caitlyn E. Seim, Decatur, GA (US); Allison M. Okamura, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 315 days.

(21) Appl. No.: 17/192,104

(22) Filed: Mar. 4, 2021

Related U.S. Application Data

(60) Provisional application No. 62/985,423, filed on Mar. 5, 2020.

(51) Int. Cl.
*A61B 5/22* (2006.01)
*A61B 5/00* (2006.01)
(Continued)

(52) U.S. Cl.
CPC ............ *A61B 5/225* (2013.01); *A47G 9/1027* (2013.01); *A61B 5/742* (2013.01); *G16H 20/30* (2018.01);
(Continued)

(58) Field of Classification Search
CPC ..... A61B 5/225; A61B 5/742; A61B 2505/09; A61B 2562/0247; G16H 20/30; A47G 9/1027
See application file for complete search history.

(56) References Cited

U.S. PATENT DOCUMENTS

| 5,735,776 A | 4/1998 | Swezey |
|---|---|---|
| 9,028,258 B2 | 5/2015 | Burdea |

(Continued)

FOREIGN PATENT DOCUMENTS

| CN | 102138860 | 8/2011 | |
|---|---|---|---|
| KR | 101929347 B1 * | 12/2018 | ............. A61B 5/225 |

OTHER PUBLICATIONS

Alavi et al. Polymeric Pressure Cushions for Potential Application on Forearm Robotic Orthoses. Simon Fraser University 2017. M.S. Thesis.

*Primary Examiner* — Devin B Henson
*Assistant Examiner* — Jonathan M Haney
(74) *Attorney, Agent, or Firm* — LUMEN PATENT FIRM

(57) ABSTRACT

Survivors of central nervous system injury commonly present with spastic hypertonia. The affected muscles are hyperexcitable and can display involuntary static muscle tone and an exaggerated stretch reflex. These symptoms affect posture and disrupt activities of daily living. Symptoms are typically measured using subjective manual tests such as the Modified Ashworth Scale; however, more quantitative measures are necessary to evaluate potential treatments. The hands are one of the most common targets for intervention, but few investigators attempt to quantify symptoms of spastic hypertonia affecting the fingers. An Isometric Force Pillow (IFP) is provided herein to quantify involuntary grip force. This lightweight, computerized tool provides a holistic measure of finger flexion force and can be used in various orientations for clinical testing and to measure the impact of assistive devices.

11 Claims, 4 Drawing Sheets

(51) Int. Cl.
    *G16H 20/30*     (2018.01)
    *A47G 9/10*     (2006.01)

(52) U.S. Cl.
    CPC ... *A61B 2505/09* (2013.01); *A61B 2562/0247* (2013.01)

(56) References Cited

U.S. PATENT DOCUMENTS

| | | | |
|---|---|---|---|
| 2011/0284004 A1* | 11/2011 | Silver | A61M 16/0003 128/205.13 |
| 2013/0345603 A1 | 12/2013 | Pienaar | |
| 2017/0368413 A1 | 12/2017 | Shavit | |
| 2018/0361596 A1 | 12/2018 | Beri | |
| 2019/0060099 A1* | 2/2019 | Ciocarlic | A41D 19/00 |
| 2021/0275074 A1* | 9/2021 | Freehill | A61B 5/0022 |

* cited by examiner

DEVICE AND METHOD TO ASSESS HAND FLEXION TONE

CROSS-REFERENCE TO RELATED APPLICATIONS

This application claims priority from U.S. Provisional Patent Application 62/985,423 filed Mar. 5, 2020, which is incorporated herein by reference.

FIELD OF THE INVENTION

This invention relates to devices and methods to assess muscle tone.

BACKGROUND OF THE INVENTION

Survivors of central nervous system injury often present with spastic hypertonia (involuntary muscle tone and spasticity). Abnormal supraspinal drive post-injury leads to motoneuron hyperexcitability, resulting in involuntary muscle contractions that can impact posture and limit range of motion. During passive movement, the limb can show an exaggerated stretch reflex as a function of movement velocity (spasticity). At rest, the limb is commonly bent or flexed from static muscle tone (hypertonia). When the upper limb is affected, symptoms may cause pain and prevent activities of daily living such as hand washing and dressing.

A variety of treatment options are used clinically, including splints, pharmaceuticals, and surgical interventions. Other treatments are for example therapeutic stimulation and robotic devices. The quantification of symptoms is both clinically and scientifically relevant. However, most therapists and investigators still rely on manual ratings that can be highly subjective. The most common measure, the Modified Ashworth Scale (MAS), is known to be subjective and have poor intra- and inter-rater variability. Other measures like the Modified Tardieu Scale (MTS) have also been shown to have high variability.

Some tools have been developed to quantitatively assess symptoms, but much of this work focuses on the limb's response to imposed movement. The affected muscle is stretched at constant velocities by a therapist or machine while joint angle is recorded using robotic devices, fiber optic tools, or marker tracking. Simultaneously, stiffness is measured through EMG, torque sensors, or load cells. Although such tools that move the limb can provide data on spasticity, imposed movement is relatively uncommon in daily life. Since the limb is often at rest, measurement of static symptoms (such as contorted posture or involuntary muscle torque) could provide useful data.

Most work on quantifying spastic hypertonia focuses on the elbow, knee, or ankle joints; yet the hands are one of the most common areas for intervention. Hand function is key to performing many tasks of self-sufficiency, and unchecked hypertonia in the hands can lead to secondary problems. Thus, measuring the level of spastic hypertonia on the hands is particularly important. However, the fingers are particularly difficult to analyze due to their many degrees of freedom. Actuating each finger or all the phalanges together is challenging due to different phalanx bone lengths. The fingers can also be difficult to secure to a device in the presence of hypertonia. The present invention addresses these concerns and provides technology to quantitatively measure involuntary hand flexion due to spastic hypertonia.

SUMMARY OF THE INVENTION

The Isometric Force Pillow (IFP) of this invention provides a holistic, quantitative measure of involuntary finger grip due to spastic hypertonia. The IFP measures static flexion force from the fingers. Since static flexion leads to many secondary problems in spastic hypertonia, the IFP provides valuable data that might also indicate problems such as difficulty to access and clean the palm and the progression of contractures. The IFP could also be used to evaluate involuntary grip when using assistive devices or pharmacological interventions to relieve hypertonia.

Circumstantial factors must always be controlled when measuring muscle tone and spasticity. Arm position is one such factor and measurement using the IFP in a standardized, gravity-neutral position is optimal. Those with difficulty achieving a standardized arm position due to severe hypertonia can get repeated measures using the IFP to provide intrasubject trend, which is because the IFP is not attached to any rigid mount or structure. The pillow is tethered only by a tube and thus can be moved freely in many positions.

In one embodiment, the invention is a device to assess hand flexion from hypertonia or hand contraction. The device can be used for hand flexion caused by (muscle) tone, hypertonia, spastic hypertonia, the flexion synergy, or contractures (tissue changes including tendon shortening—not necessarily muscle tone). The device has a cylindrical or rectangular inflatable pillow. The pillow can be set to an internal air pressure. The pillow is sized for a hand such that the fingers and the thumb of the hand can be wrapped around the pillow and simultaneously compress the pillow. The pillow is wide enough, or has a large enough diameter so that the fingers and thumb do not touch either in compression state or non-compression state. The compression results in a change of the internal air pressure. The device further distinguishes an air pressure sensor for sensing the internal air pressure.

An air pressure convertor converts the air pressure changes into therapeutic meaningful values. The device could also have a display to the display the therapeutic meaningful values and provide feedback to the user and/or healthcare professional.

The device could have a programmed translation/conversion of the air pressure sensor readings into therapeutic meaningful values like e.g. unit force measurements, scales like the Ashworth scale, custom scales, or the like. This could be programmable software code readable and executable by a computer device to convert the air pressure changes into these desired values.

In a variation of the device embodiment, the cylindrical or rectangular inflatable pillow could have a plurality of individual air chambers each connected with an air pressure sensor capable of reading the respective internal air pressure changes.

In another embodiment, the invention is a method to assess (involuntary) hand flexion from hypertonia or hand contraction. Likewise, as to the device, the method can be used for, and measure symptoms of, hand flexion caused by (muscle) tone, hypertonia, spastic hypertonia, the flexion synergy, or contractures (tissue changes including tendon shortening—not necessarily muscle tone). With the device as described above, a user has placed his/her hand around the pillow. Voluntary or involuntary compression caused by the fingers and/or thumb of the pillow causes internal air pressure changes. The internal air pressure changes caused by the compression are sensed by a pressure sensor. An air pressure to unit force convertor converts the air pressure changes into therapeutic meaningful values. The therapeutic meaningful values could be displayed to provide feedback to the user and/or healthcare professional.

The conversion could have a programmed translation/conversion of the air pressure sensor readings into therapeutic meaningful values like e.g. unit force measurements, scales like the Ashworth scale, custom scales, or the like. This could be programmable software code readable and executable by a computer device to convert the air pressure changes into these desired values.

Embodiments of the invention have at least the following advantages in view of prior methods and device:
- Quantification of measurements in contrast of subjective ratings by a therapist.
- Remote measurements are feasible.
- No human proctor needed.
- Use of rectangular or cylindrical pillow shape allows all fingers to extend and ensures each digit has equivalent space to compress within the pillow.
- No imposed movement of a joint by actuators or a human, but the IPF obtains meaningful information without actuating the limb.
- IFP device can be used with minimal setup and can provide a holistic value.
- IFP tool is self-contained, tethered only by a flexible tube, and thus can produce force readings for patients who cannot fit their arms into standard, rigid apparatus.

DETAILED DESCRIPTION

The objective of this invention was to develop a method and device to measure symptoms of spastic hypertonia in the hands, to provide quantitative data when studying treatment efficacy. Spastic hypertonia often causes the finger flexors to contract, so measuring flexion force is an accepted strategy.

The device was intended to be low-cost and compact to promote perceived ease of use. In early state prototypes, a hinge-like design was used that measured finger flexion using a load cell—aiming to expand the Wrist Finger Torque Sensor into a stand-alone design with a focus on the fingers. When these prototypes were tested on stroke survivors with upper-limb hypertonia, the fingers were difficult to secure even using straps. Like other tools the hinge had to be mounted on a rigid surface. If the individual's elbow or wrist was contracted, their hand could not reach the tool. Those with moderate to severe spastic hypertonia could not use the prototypes. This design was also only capable of measuring force at the MCP joints.

Figure 1:
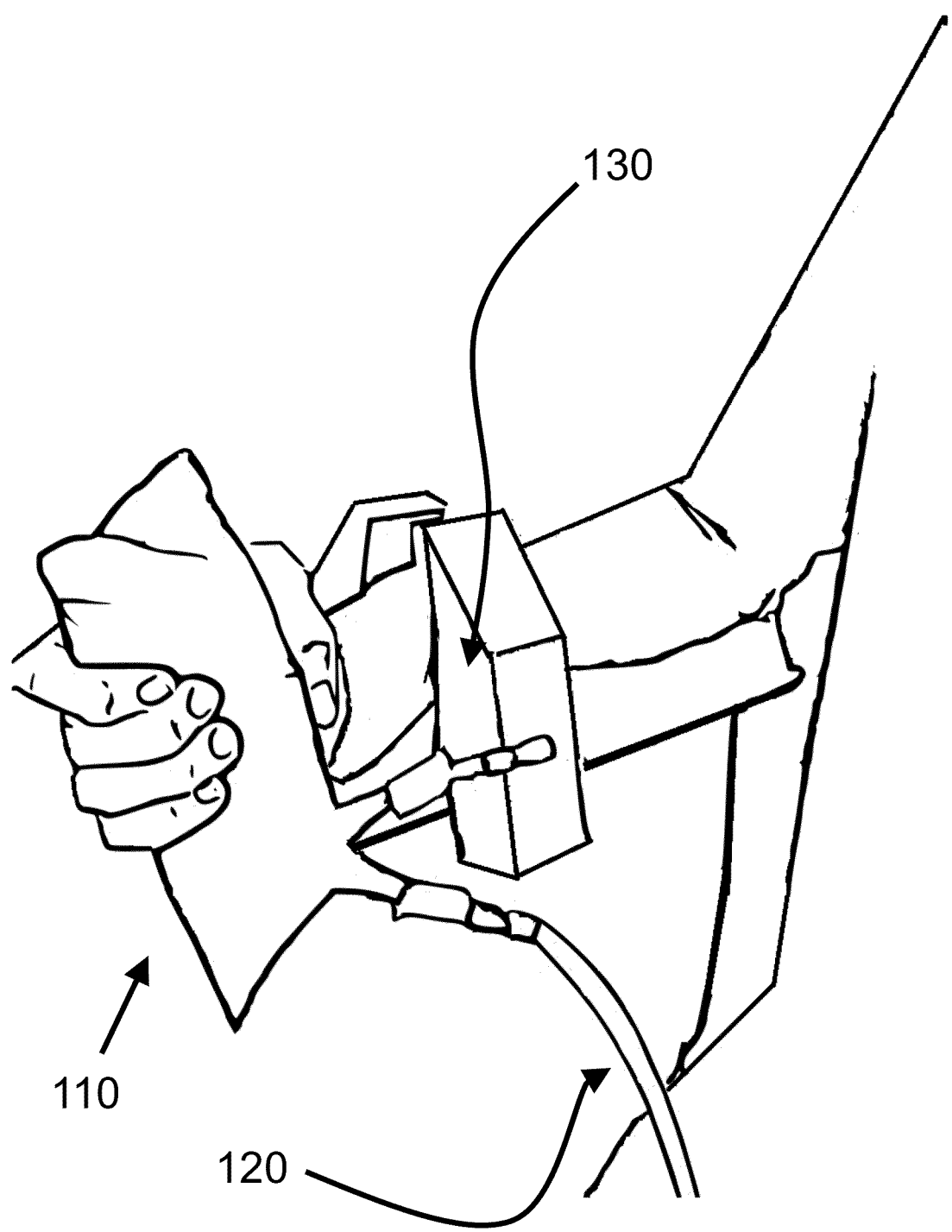
FIG. 1 shows according to an exemplary embodiment of the invention the Isometric Force Pillow (IFP) 110 used in a gravity-neutral position. The tube 120 leads to the pressure sensor 310 shown in FIG. 3. The other valve 130 is clamped after initial inflation using a hand vacuum pump.

In an exemplary embodiment of the invention, the hinge design was replaced with a graspable cushion (FIG. 1), the isometric force pillow (IFP, 110). The IFP has an ergonomic form and is designed to fit into the hand. The IFP uses air pressure to measure finger flexion force, which provides a holistic measure of contraction at multiple joints. This self-contained device and method of measuring force does not require attachment to a rigid mount and thus allows the unit to be free-moving. It is capable of being used both in the gravity-neutral position and in other orientations. The IFP is tethered only by a flexible tube.

Mechanical Design

In one example, IFP 110 is 8 inches in length by 4 inches in diameter when not inflated. These dimensions allow fingers of various lengths to be extended when grasping IFP 110, without allowing the thumb and fingertips to touch. The shape of IFP 110 is rectangular or cylindrical, however it is not tapered. This is in contrast to an orthotic device for hypertonia, such as the Hand Contracture Carrot Orthosis (AliMed, Inc.), which is explicitly designed in a tapered shape so that it can slide into the hand. Tapered or ball shapes will not provide an equitable measure of force from all the fingers. For instance, the fifth digit (little finger) could slide off of a ball shape or would not exert much force onto the bladder. In a tapered form or other forms, the fingers would be held at varying degrees of extension. This would result in unequal measures across the fingers, neglecting some of the most affected parts of the hand (e.g. digits four and five often have increased contraction and thus measurement is essential).

IFP 110 ensures equal extension of the fingers by using a symmetrical, rectangular or cylindrical design. This design could also be augmented by adding ergonomic indentations for each finger and the thumb, or a 4- or 2-chambered bladder which could read the pressure at each finger; or between the second/third digits, and the fourth/fifth digits which often express increased symptoms and are controlled by different nerves.

Figure 2A:
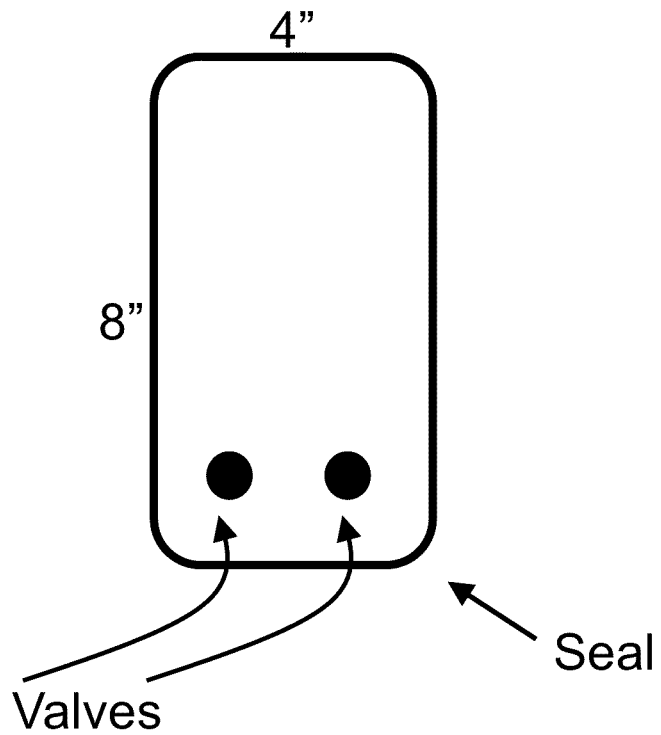
FIGS. 2A-B show according to an exemplary embodiment of the invention the assembly of the IFP.
Figure 2B:
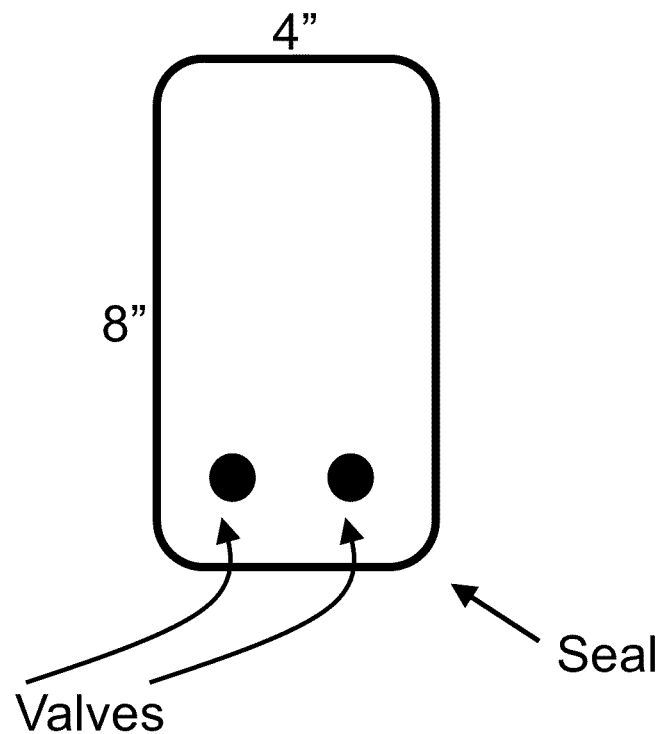
Figure 2B:
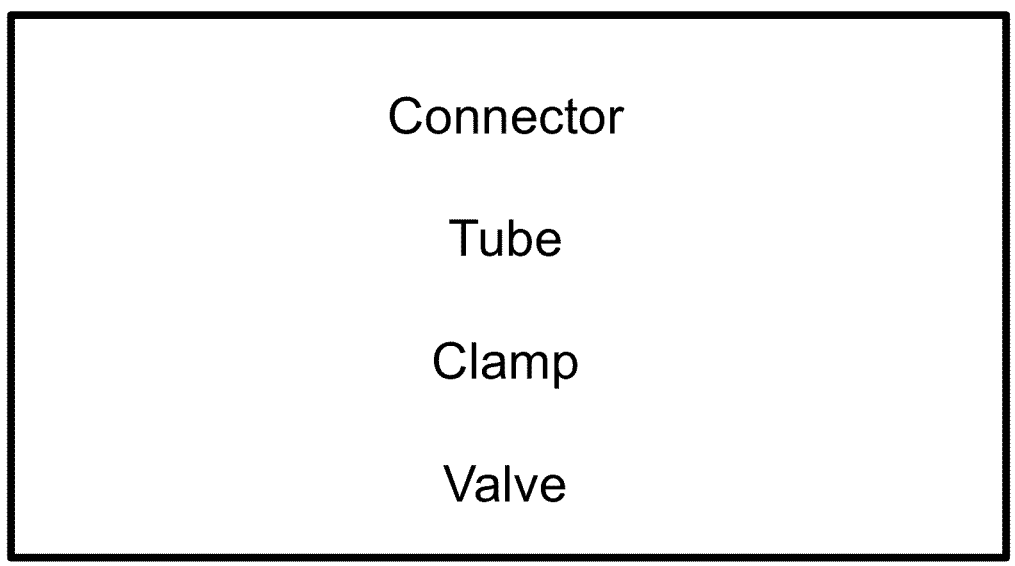

Air pressure in IFP 110 is maintained to provide an accurate differential pressure measurement. As an example, an airtight seal could be created in an 8-step process (FIGS. 2A-B). Four-mil heavy duty polyethylene tubing cut at a length of 8 inches forms the inner layer of the cushion. Two air-tight valves are assembled using through-wall connectors (5779K677, McMaster-Carr). Holes of ¼" diameter are cut in the polyethylene tubing and double-sided VHB acrylic tape (S-10123, Uline) is applied surrounding each hole. ¼" rubber O-rings are placed on both the inside and the outside of the polyethylene tubing, and the through-wall connectors are twisted shut. After the valves are in place, a tabletop impulse sealer (H-163, Uline) seals the polyethylene tubing.

A sheet of silicone-coated ripstop nylon (FRCS, Seattle Fabrics Inc.) is cut to wrap over the polyethylene tubing and is sealed on by the tabletop impulse sealer. The nylon material adds friction to prevent slippage while the IFP is in use. It also prevents the polyethylene tubing from stretching during inflation and squeezing, and prevents bursting. Four inches of ¼" soft plastic tubing attaches to each valve and a mini tubing clamp (59199, U.S. Plastic Corp.) is added so each valve could be sealed. One of these tubes attaches to a pressure sensor using a straight tube connector (5779K14, McMaster-Carr). The other tube is used to inflate the cushion via a hand vacuum pump (e.g. MV8255, Mityvac, or any other pump or bulb). After inflation, the pump could be disconnected and the tube is clamped, but could also left attached.

Electronics and Software

Figure 3:
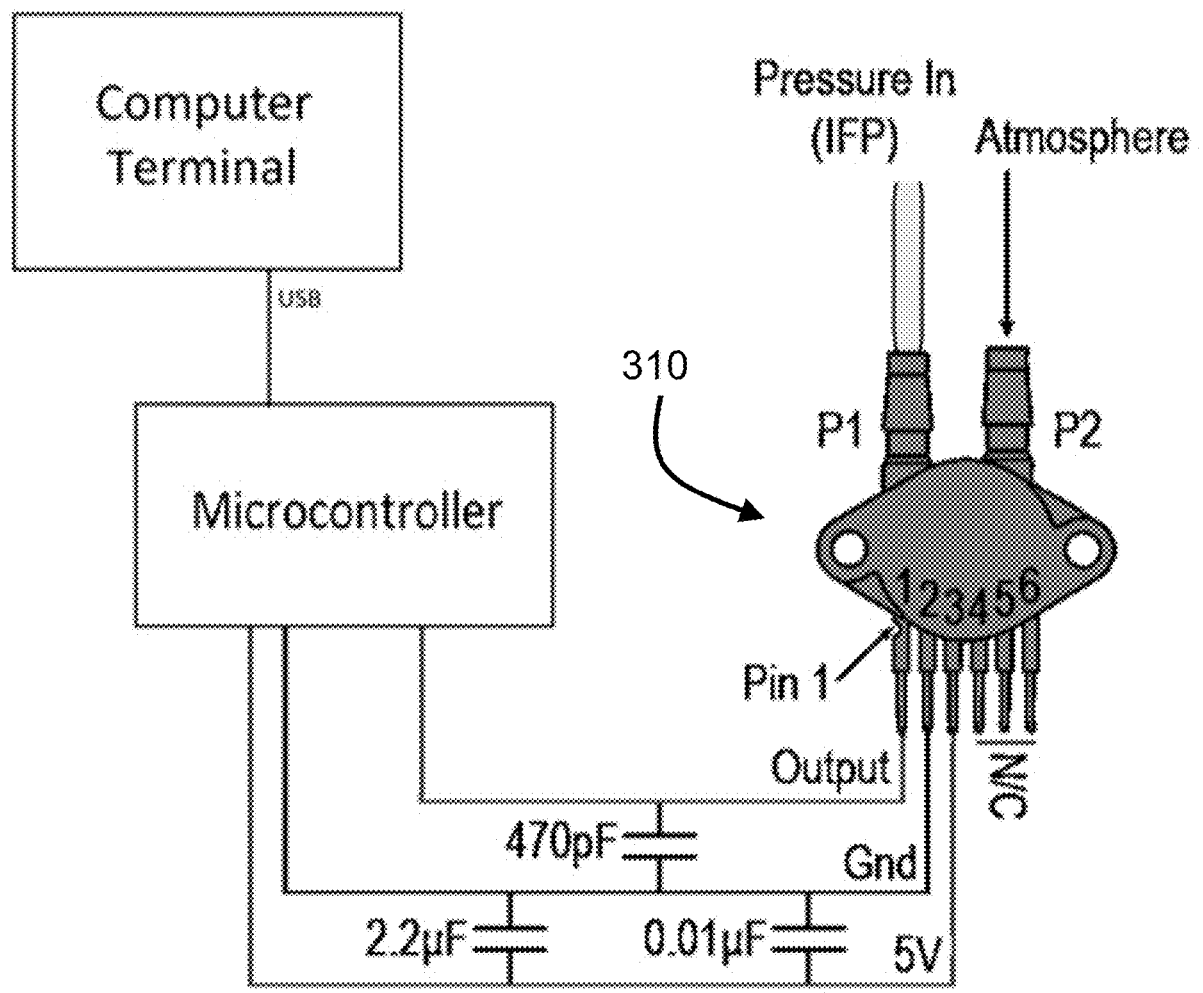
FIG. 3 shows according to an exemplary embodiment of the invention schematic of the IFP electronics.

As an example, a differential pressure sensor 310 (e.g. MPX5050-DP, NXP Semi-conductors) measures pressure within the IFP and can detect small changes in grip (<0.1 PSI). One port (P1) on the sensor connects to the IFP valve via soft tubing. The other port (P2) is exposed to atmospheric pressure. The power, ground, and output voltage pins on the sensor connect to a microcontroller (e.g. Arduino Duemilanove) using a 3-wire ribbon cable. The circuit board houses a power supply decoupling and output filtering circuit (FIG. 3).

A custom script converts the analog voltage from the sensor into gauge pressure readings at 5 Hz-10 kHz. The sensor readings are calibrated by subtracting a constant offset. The offset was empirically measured with both sensor ports P1 and P2 exposed to atmospheric pressure. The calibrated pressure values could be smoothed using, in one example, and not limiting to the invention, a moving average filter with a sample size of 10. The pressure reading is then displayed on a computer terminal for clinicians or investigators.

The device can display the value in a unit of force (N, PSI, kPA) within a range of 0-95 PSI using a digital sensor. For those with moderate function, a range of 0-5 PSI can be sufficient to measure symptoms, and the IFP can achieve precision of 0.25 PSI using only a mechanical gauge. The IFP could also be used to display common language ratings (e.g. severe finger flexion force, moderate, mild, low, and normal/none); indications of symptoms (e.g. risk of damage to the palm, risk of pain, difficulty in hygiene); and associated/analogous levels of standardized measures of spastic hypertonia determined through experimentation (e.g. ratings of the Modified Ashworth scale or Modified Tardieu scale).

Examples of Measurements

Seat the participant
Place the arm as close to the neutral-gravity position as possible using the brace
  Elbow between 80-110 degrees
  Wrist close to 180 (0) degrees
  No external or internal shoulder rotation
  Shoulder is not abducted, or flexed beyond 30 degrees
  Document angles when neutral position is not achieved
Document
  Laboratory temperature
  Time of Baclofen dose today
  Time of glove use today
Place the pillow in the hand with sensor leads facing outwards near the base of the palm
Normal Arousal Measures—Involuntary Hand Flexion Force at Random Arousal Levels:
  Place the pillow in the hand at the designated 3 times during the experiment visit
    (in between other measurement tasks: Semmes-weinstein monofiliment exam, and anecdotal video clips)
High Arousal Measures—the Inability to Release the Grasp:
  Have the seated participant attempt the Jendrassik maneuver for 5 seconds
  Have the seated participant attempt to squeeze their hands into fists for 5 seconds
  Have the participant relax their hands as if to open and release their grasp for 5 seconds
  Take pillow measurement of remaining involuntary grip force
  Repeat 3 times
Relaxed Measure—after Ramp Stretches:
After 3 minutes of manual ramp stretches of the affected hand, recorded on camera/EMG, while the patient relaxes as if going to sleep
Take pillow measure

What is claimed is:

1. A device to assess hand flexion from hypertonia or hand contraction, comprising:
   (a) a cylindrical or rectangular inflatable pillow having an internal air pressure of the entire internal air volume of the cylindrical or rectangular inflatable pillow, wherein the cylindrical or rectangular inflatable pillow is sized for a hand such that the fingers and the thumb of the hand can be wrapped around the pillow and simultaneously compress the pillow, wherein the cylindrical or rectangular inflatable pillow is further sized so that the fingers and thumb do not touch in a compression state or a non-compression state of the cylindrical or rectangular inflatable pillow, whereby the compression results in a change of the internal air pressure, wherein the cylindrical or rectangular inflatable pillow has an air output connected to a flexible hollow tubing for allowing passage of the air;
   (b) an air pressure sensor for sensing the internal air pressure of the entire internal air volume of the cylindrical or rectangular inflatable pillow, wherein the air pressure sensor is connected to the flexible hollow tubing allowing passage of the air to the air pressure sensor and as such connected to the cylindrical or rectangular inflatable pillow, and wherein the air pressure sensor by connection via the flexible hollow tubing is located at a distance and externally from the cylindrical or rectangular inflatable pillow;
   (c) an air pressure convertor to convert the air pressure changes into therapeutic meaningful values; and
   (d) a display to the display the therapeutic meaningful values.

2. The device as set forth in claim 1, wherein the air pressure convertor comprises programmable software code readable and executable by a computer device to convert the air pressure changes into the therapeutic meaningful values.

3. The device as set forth in claim 1, wherein the therapeutic meaningful values are unit force measurements, Ashworth scale values or a custom scale.

4. The device as set forth in claim 1, wherein the cylindrical or rectangular inflatable pillow has a plurality of individual air chambers each connected with an air pressure sensor capable of reading the respective internal air pressure changes.

5. The device as set forth in claim 1, wherein the air pressure sensor is a differential air pressure sensor.

6. The device as set forth in claim 1, wherein the air pressure convertor converts analog voltage from the air pressure sensor into gauge pressure readings at 5 Hz to 10 kHz.

7. A method to assess hand flexion from hypertonia or hand contraction, comprising:
   (a) having a cylindrical or rectangular inflatable pillow with an internal air pressure of the entire internal air volume of the cylindrical or rectangular inflatable pillow, wherein the cylindrical or rectangular inflatable pillow is sized for a hand such that the fingers and the thumb of the hand can be wrapped around the pillow and simultaneously compress the pillow, wherein the cylindrical or rectangular inflatable pillow is further sized so that the fingers and thumb do not touch in a compression state or a non-compression state of the cylindrical or rectangular inflatable pillow, whereby the compression results in a change of the internal air pressure wherein the inflatable pillow has an air output connected to a flexible hollow tubing for allowing passage of the air;

(b) sensing the internal air pressure of the entire internal air volume of the cylindrical or rectangular inflatable pillow caused by the compression with an air pressure sensor, wherein the air pressure sensor is connected to the cylindrical or rectangular flexible hollow tubing allowing passage of the air to the air pressure sensor and as such connected to the cylindrical or rectangular inflatable pillow, and wherein the air pressure sensor by connection via the flexible hollow tubing is located at a distance and externally from the inflatable pillow;

(c) converting the sensed air pressure changes into therapeutic meaningful values; and (d) displaying the therapeutic meaningful values.

8. The method as set forth in claim 7, wherein the air pressure convertor comprises programmable software code readable and executable by a computer device to convert the air pressure changes into the therapeutic meaningful values.

9. The method as set forth in claim 7, wherein the therapeutic meaningful values are unit force measurements, Ashworth scale values or a custom scale.

10. The method as set forth in claim 7, wherein the air pressure sensor is a differential air pressure sensor.

11. The method as set forth in claim 7, wherein the converting step comprises converting analog voltage from the air pressure sensor into gauge pressure readings at 5 Hz to 10 kHz.

* * * * *